United States Patent [19]

Reuter

[11] Patent Number: 5,578,111

[45] Date of Patent: Nov. 26, 1996

[54] PROCESS AND A DEVICE FOR CONTINUOUS CHROMATOGRAPHY

[75] Inventor: Karl A. Reuter, Freiburg, Germany

[73] Assignee: Reuter Chemischer Apparatebau GmbH, Switzerland

[21] Appl. No.: 403,757

[22] PCT Filed: Sep. 17, 1993

[86] PCT No.: PCT/EP93/02583

§ 371 Date: Mar. 17, 1995

§ 102(e) Date: Mar. 17, 1995

[87] PCT Pub. No.: WO94/06532

PCT Pub. Date: Mar. 31, 1994

[30] Foreign Application Priority Data

Sep. 18, 1992 [DE] Germany .......................... 42 31 327.9

[51] Int. Cl.⁶ .......................... B01D 15/08; B01D 53/04; B01D 53/06
[52] U.S. Cl. .......................... 95/86; 95/107; 95/113; 96/104; 96/123; 96/124; 96/125
[58] Field of Search .......................... 95/82–89, 90, 95/107, 113; 96/101–107, 108, 121–125, 150

[56] References Cited

U.S. PATENT DOCUMENTS

| | | | |
|---|---|---|---|
| 3,002,583 | 10/1961 | Findlay | 95/82 X |
| 3,077,103 | 2/1963 | Heaton | 95/82 X |
| 3,078,647 | 2/1963 | Mosier | 96/105 |
| 3,187,486 | 6/1965 | Dinelli et al. | 95/86 |
| 3,257,781 | 6/1966 | Debbrecht et al. | 96/105 |
| 3,417,548 | 12/1968 | Thompson | 55/67 |
| 3,503,712 | 3/1970 | Sussman | 55/386 X |
| 3,511,028 | 5/1970 | Saylor | 55/67 |
| 3,527,350 | 9/1970 | Tuthill et al. | 96/104 X |
| 3,703,798 | 11/1972 | Pretorius et al. | 95/82 |
| 3,796,657 | 3/1974 | Pretorius et al. | 95/84 X |
| 3,856,681 | 12/1974 | Huber | 96/107 X |
| 5,139,680 | 8/1992 | Tarnopolsky | 95/82 X |

FOREIGN PATENT DOCUMENTS

| | | | |
|---|---|---|---|
| 433510 | 12/1969 | Austria . | |
| 0439753 | 1/1975 | U.S.S.R. | 96/101 |
| 0532049 | 10/1976 | U.S.S.R. | 96/105 |
| 1279736 | 6/1972 | United Kingdom | 96/101 |
| WO92/16275 | 10/1992 | WIPO . | |

Primary Examiner—Robert Spitzer
Attorney, Agent, or Firm—Burns, Doane, Swecker & Mathis

[57] ABSTRACT

A process is described for the separation of a mixture of substances by sorption of the mixture's components on two different sorption agents, which are individually and independently adjustable in their sorption properties, and is performed in a manner by which the mixture of substances to be separated is introduced into a separation chamber between the surfaces of the sorption agents, and in which the separation chamber is occupied by a gap medium, in which the mixture's components can be dissolved and/or dispersed and/or evaporated, while the phases containing the sorption agents move in opposing directions, and the separated components of the mixture held on the sorption agents are recovered after passage through the separation path. This process is characterized in that the separation chamber is formed by at least two or several hollow, concentrically superimposed cylindrical disks $Z_A$ and $Z_B$, which are filled with structural elements, and which contain separation media $Ph_A$ and $Ph_B$, consisting of or containing the sorption agents, and that the cylindrical disks $Z_A$ and $Z_B$ are alternately arranged and move around a common axis in directions opposite to each other, and in that an exchange of the gap medium and hence equilibration of the substances to be separated between the surfaces of the sorption agents occurs.

25 Claims, 5 Drawing Sheets

PROCESS AND A DEVICE FOR CONTINUOUS CHROMATOGRAPHY

DESCRIPTION

This invention concerns a process and a device for continuous chromatography (CC).

The term chromatography indicates a separation process, in which the substances to be separated can generally be separated from each other by phase distribution based on physical and chemical differences and principles, detected by suitable sensing procedures and isolated by elution. One of the phases used in chromatography is immobile (stationary) and usually has a large surface area, while the other is mobile and moves over or through the stationary phase. The stationary phase can be a solid (absorbent) or a liquid, in which latter case the immobilization of the phase and its large surface area is achieved by coating the liquid as a thin film onto a porous, small-particle carrier material. The mobile phase is generally a liquid that is not miscible with the stationary phase or a gas. Based on these differences, a distinction is usually made between liquid-solid chromatography, gas-solid chromatography and gas-liquid chromatography. Another distinction, made based on the operating separation principle, is that of adsorption and distribution chromatography; the resolution of mixtures of substances is based on the differing retention times of the individual substances on the stationary phase, and the degree of resolution depends on several factors, especially the differences in retention of the component substances on the stationary phase. The separation efficiency of a chromatography column is, to a large measure, also determined by the particle size of the stationary phase (e.g. the extent of the surface area, the band widening due to differing path lengths), and hence the so-called high-efficiency (or high pressure) liquid chromatography (HPLC) employs substantially finer grained materials (5 to 30 μm) than the gel chromatography (35 to 75 μm) or the column chromatography (120 to 200 μm). The small particle size of the adsorbents dictates, however, the use of high pressures (up to 400 bar).

Performance of the chromatography itself involves applying the mixture of substances to a confined "dot" area at the starting zone (on the column, thin layer etc.) and transporting it forward by means of the mobile phase (gas in GC, solvent in HPLC). Depending on the adsorption/desorption equilibrium of a given substance, it is migrating at a different speed through or over the stationary phase, and the maximum possible speed is that of the mobile phase.

The chromatographic processes known heretofore do, however, exhibit certain disadvantages. For instance, a continuous operation of such chromatography installations is not possible, and electronically regulated, automatic optimization during the progress of a separation is hardly meaningful, nor even feasible. When the retention times for different substances are similar, the separation achieved is often incomplete. The state of loading (capacity utilization) of the absorptive phase during preparative separation (which is equivalent to the migration zone of the as yet un-separated mixture of substances) usually represents a local overloading of the stationary phase, e.g. of a column. Full efficiency of separation is then achieved only toward the end, when the substances to be separated are already distributed over a major volume of the column, i.e. are separated already to a significant extent, while the greater portion of the adsorptive phase (that outside the migrating zone) is not even participating in the instantaneous separation process.

The distribution (equilibration) always occurs only between an adsorptive medium (stationary phase) and the eluent (mobile phase), and not between two adsorption media which can be chosen essentially without restrictions, such as e.g. between adsorption media which are suitably selected by their physical, chemical and/or chiral properties and specifically chosen for effective separation of certain substances (for example, two enantiomers, sorption media with different polarity, acidity/basicity or opposite (and adjustable) electric charges).

Additionally, the temperature of the stationary and the mobile phases is, by necessity, approximately the same, and different temperatures of the two phases cannot be adjusted/maintained.

It is the objective of the present invention to avoid the disadvantages associated with the previously known chromatography processes, and to provide a chromatographic process which is suitable for continuous operation and allows electronically regulated, automatic optimization, and which makes possible a rapid, potentially continuous and effective separation of substances, based on unrestricted choice of the various separation phases and their physical, chemical and/or chiral conditions selected specifically for given substances, while at the same time, this process is also operable on a preparative or industrial scale.

PCT-Application WO 92/16275 of the present applicant describes a process for the separation of a mixture of substances by sorption of the mixture's components on two different sorption media. Their sorption properties are adjustable independently and individually to the specific mixture of substances, by appropriate choice of charge, polarity, chiriality, temperature, void space size, viscosity etc., and the individual components of the mixture are bonded with differing strengths depending on their physico-chemical or steric (chiral) properties. The process disclosed there is characterized in that the mixture of substances to be separated is introduced into the separation chamber between two surfaces of the sorption agents, a medium being present in the space between opposing surfaces of the sorption agents, into which the mixture's components can be dissolved and/or dispersed and/or evaporated, and in which at least two of the three phases formed by the surfaces and the gap medium are moving in opposite direction and essentially constant distance to each other, and in which the separated components of the mixture held on the sorption agents after passage through the separation zone are recovered by desorption or elution.

According to that process, it is possible to make unrestricted choices of certain properties, such as e.g. the type, speed and temperature of the individual phases, and adjust them selectively to the mixture to be separated.

It has now been found that the results obtained with the process and device of WO 92/16275 can be improved significantly in respect to the stated objectives, especially in respect to an optimization of separation, simple mode of operation also on an industrial scale and broad applicability of the process, when the process and device according to the present invention is applied, i.e. when the separation chamber for the mixture of substances to be separated is of a configuration formed by at least two or several hollow cylindrical disks $Z_A$ and $Z_B$, which are filled with structural elements and concentrically superimposed, and the cylindrical disks $Z_A$ and $Z_B$ being alterately arranged and rotating around a common axis in directions opposite to each other.

The process according to this invention, for the separation of a mixture of substances by sorption of the mixture's components on two different sorption agents, which are individually and independently adjustable in their sorption properties, is performed in a manner by which the mixture of substances to be separated is introduced into the separation chamber (3) between the surfaces of the sorption agents (1, 2), and in which the separation chamber (3) is occupied by a gap medium, in which the mixture's components can be dissolved and/or dispersed and/or evaporated, while the phases containing the sorption agents move in opposing direction, and the separated components of the mixture held on the sorption agents are recovered after passage through the separation path. This process is characterized in that the separation chamber (3) is formed by at least two or several hollow, concentrically superimposed cylindrical disks (134, 135) $Z_A$ and $Z_B$, which are filled with structural elements, and which contain the separation media $Ph_A$ and $Ph_B$, consisting of or containing the sorption agents (1, 2), and that the cylindrical disks $Z_A$ and $Z_B$ are alternately arranged and move around a common axis in directions opposite to each other, and in that an exchange of the gap medium and hence equilibration of the substances to be separated between the surfaces of the sorption agents (1, 2) occurs. The rotational speed of the cylindrical disks $Z_A$ moving in one direction is normally the same as that of those $Z_B$, turning in the other direction.

Suitable sorption agents (1, 2) are those described also in PCT-Application WO 92/16275, and their sorption properties can be adjusted individually and independently to the specific mixture of substances by suitable choice of charge, polarity, chiriality, temperature, void space size, viscosity etc., and the individual mixture components are bonded with different strengths depending on their differing physico-chemical or chiral properties.

The cylindrical disks $Z_A$ and $Z_B$ preferentially have an outer diameter of 5 to 5000, and especially 50 to 2000 mm; their height (thickness) is preferentially 0.1 to 2000 mm, and especially 1 to 500 mm.

One possibility to produce a rapid exchange of the mixture of substances on the separation medium $Ph_A$ with the mixture of substances on the separation medium $Ph_B$, and thus an effective equilibration between the two separation media, is given in the staking of several cylindrical disks with $Ph_A$ and a corresponding number of cylindrical disks with $Ph_B$, each of relatively small thickness and arranged in alternation and concentrically on one axis. At very small thicknesses, a sufficiently rapid exchange is provided by diffusion. With thicker cylindrical disks, this arrangement allows a significant shortening of the time that is required for recirculation of the gap medium and thus equilibration between the two phases $Ph_A$ and $Ph_B$. The number of superimposed, stacked cylindrical disks $Z_A$ and $Z_B$ is preferentially 2 to 10000, and especially 2 to 200.

All cylindrical disks $Z_A$ turn in the same direction and usually at the same speed, just as all cylindrical disks $Z_B$ turn in the same, but opposite direction, and usually at the same speed. The rotational speeds of $Z_A$ and $Z_B$ may be different from each other, but are preferably the same. The preferred turning rate is 1 rpd (rotation per day) to 10 rpm.

The efficiency of the process according to this invention (3-phase-counter current chromatography) depends significantly on an effective exchange of the gap medium, and thus of the mixture of substances between the separation agents (separation phases) $Ph_A$ and $Ph_B$. In this, however, it is important that the mixture of substances to be equilibrated is not substantially transported in the direction toward the discharge locations for the pure components ($ATO_A$ and $ATO_B$), while it moves between the phases $Ph_A$ and $Ph_B$.

According to the invention, it is hence advantageous to fill the cylindrical disks $Z_A$ and $Z_B$ with structural elements. In this, the following two configurations are especially suitable forms for such structural elements:

(A) Filling of the cylindrical disks with structural elements in arrangement parallel to the axis;

(B) Subdivision of the cylindrical disks $Z_A$ and $Z_B$ into essentially matching segments, with concentric and equidistant arrangement, e.g. in the form of pie-sectors or circular segments, with circular segments being preferred.

Examples for structural elements with axio-parallel arrangement for the filling of the cylindrical disks are especially fibers and small rods, preferably with a diameter of 0.05 μm to 5 mm and especially 0.1 μm to 1 mm; capillaries, thin tubes, perforated plates or weaves, such as e.g. glass fiber cloth or glass frittes, where the inner diameter of the capillaries, thin tubes and perforations is preferably 0.1 μm to 10 mm, and especially 1 μm to 5 mm; also lamellae in essentially coplanar arrangement to the family of planes including the axis, with the distance between neighboring lamellae being preferably 0.1 μm to 10 mm, and especially 0.5 μm to 5 mm, and the preferred number of lamellae being 5 to 1,000,000, and especially 24 to 12,000.

The diameter of the axio-parallel structural elements (as outlined in (A)), e.g. the fibers or capillaries, or the distance between neighboring lamellae is preferably chosen such as to minimize the possibility of a lateral drift during frequent exchange of the gap medium between cylindrical disks $Z_A$ and $Z_B$. This lateral drift can be especially high e.g., when the diameters of the axio-parallel structural elements, e.g. the capillaries or lamellae, only incompletely cover the packing gaps in the adjacent cylindrical disk when sliding over it. One possibility for the preparation of perforated plates lies e.g. in lateral gluing (filling of the gaps) of the axio-parallel structural elements, e.g. by coating with an adhesive resin etc., and the materials effecting lateral bonding may themselves also act as sorption agents (1, 2). As a rule, the axio-parallel structural elements, such as e.g. fibers, small rods, capillaries and thin tubes and lamellae, are coated with the sorption agents, but may even consist of these sorption agents when suitably chosen.

The structural elements named under (B) in the preceding in the form of segments are especially preferred according to the invention.

The number of segments per cylindrical disk is preferably from 2 to 500, and especially 4 to 128.

The segments may be filled with the structural elements described under (A) in the preceding, such as e.g. fibers, capillaries and/or lamellae, and here also, axio-parallel arrangement is beneficial, or with particulate separation and/or carrier materials, consisting of or bearing on their surfaces the sorption agents.

Suitable carrier materials or separation materials (sorption agents) for the structural elements described under (A) and (B) and/or their fillers are essentially all the carrier and separation materials customary in column chromatography, and especially those carrier and separation materials described in PCT Application WO 92/16275. Especially suitable are particulate or fibrous carrier materials bearing the sorption agents on their surfaces.

It is preferred that the carrier and separation materials used according to this invention have a somewhat larger particle size than the materials used in conventional column chromatography. This assures easy passage of liquid and thus short equilibration times.

According to this invention, frequently used are silica gels, sand, diatomaceous earth, calcined clay, polymeric particles, polymeric fibers, e.g. cotton, wool, nylon fibers, glass wool, capillary tubes e.g. of glass or organic polymer, and/or glass beads. The diameter of the silica gels is to advantage at 5 to 1000 µm, and especially at 10 to 500 µm; the diameter of the sands used at 20 to 5000 µm, and especially 50 to 2000 µm; and the diameter of the glass beads at 10 to 2000 µm, and especially 20 to 500 µm.

The rotation of the cylindrical disks may be made continuous or discontinuous; the choice between the two modes of rotation depends primarily on the configuration and arrangement of the structural elements: When the disks are filled with structural elements in axio-parallel arrangement, rotation is done to advantage at a constant speed, i.e. continuously, while a discontinuous rotation is required when segments are used (as in one of the previously described configurations (B)). In this case, the cylindrical disks $Z_A$ and $Z_B$ are in a stationary, superimposed position during the rest period (equilibration phase), such that the segments (segment walls) are exactly matching up on top of each other, and thus all segments or perforations form continuous channels through the entire stack of cylindrical disks $Z_A$ and $Z_B$. A sufficient degree of tightness of these channels toward the neighboring channels is achieved e.g. by adequately wide sealing surfaces (segment walls) of the segments, adequately low free-play between the cylindrical disks $Z_A$ and $Z_B$, appropriately low pressure in the transport medium, and/or special features (O-ring gaskets, rubber-, silicone-, or Teflon®-seals, compression during the equilibration phase, etc.). When the cylindrical disks $Z_A$ and $Z_B$ contain very many segments and the segment walls are consequently thinner, elastic lip seals or gaskets etc. may also be affixed to the edges of the segments.

The mixture of substances to be separated is best introduced by a suitable charging system, e.g. by an air stream which can be loaded with a defined quantity of gaseous mixture of substances to be separated. This can be accomplished, e.g. in a column filled with Raschig rings and a top-to-bottom trickle of the liquid mixture to be separated at a defined temperature, while a defined quantity of air per time unit flows from the bottom upwards.

Discharging of the components (fractions) of the separated mixture of substances from the sorption agents is conveniently done with a suitable discharge system, e.g. a gas stream, into which the separated components evaporate from the adsorption surface, and from which they are condensed in one (or several in series, if so needed) cold trap.

In principle, one of the processes or devices described in WO 92/16275 can be utilized as the charging and discharging systems. However, according to this invention, it is more beneficial to use the stationary cylindrical disks 191, 192 as part of the charging and/or discharging system.

Thus e.g., cylindrical charging disks 191 and cylindrical discharging disks 192 can be installed between the individual cylinder disks $Z_A$ and $Z_B$ in the cylinder stack. These have the same segmentation as the cylindrical disks $Z_A$ and $Z_B$, but are not filled and/or charged with sorption agent (separation material) and are not moved during the separation process. Those segments in 191 and 192, through which the mixture of substances is introduced or withdrawn along with the gap medium, namely then the segments between the charging and discharging locations, block the free passage of one segment in the cylindrical disk $Z_A$ to its opposite segment in cylinder disk $Z_B$, and are fitted with inlet and/or outlet adaptors. In this way, each charging and/or discharging segment of 134 and 135 can be filled or emptied individually. All other segments of the disks 191, 192 conduct the gap medium with the material to be separated from one segment each of the cylindrical disk $Z_A$ into its opposing segment in cylindrical disk $Z_B$.

For achieving a yet better separation of the mixture of components, e.g. components A and B, it is advantageous according to this invention to feed the component A to that segment located opposite to the discharge location $ATO_A$ for component A, and correspondingly feed component B to that segment located opposite to the discharge location $ATO_B$ for component B.

While, e.g. the component A of the separated mixture from A+B is discharged at location $ATO_A$ from the cylindrical disk $Z_A$ (with separation medium $Ph_A$), the opposing segment of cylindrical disk $Z_B$ with the separation medium $Ph_B$ can be partially charged with component A. The analogous operation applies to discharge location $ATO_B$. The following effects can be achieved with this operational modification:

1. Levelling of the loading over the entire length of the separation section: Without the final feed-back of the components A and/or B, the concentration on $Ph_A$ and $Ph_B$ is distinctly lower at the end of the separation section than at its start, with the feed-back addition of the components A and B occurring at $ATO_A$ and $ATO_B$. This effect is especially pronounced at low differences in occupation, which can be explained in the following manner: Assuming that $Ph_A$ and $Ph_B$ are each loaded in the middle at 100% with a mixture of 50% A and 50% B, and the distribution coefficient "a" (amount of component A on unit volume $Ph_A$ in ratio to amount of component B on unit volume $Ph_B$) is 0.52, then 52% of the quantity of A present in the preceding chamber ($ATO_A$–1) can be withdrawn in the last distribution step only if the substance was nearly 100% pure in the penultimate step. Calculations actually show, for five distribution steps (n=5) from the middle $ETO_A$–$ETO_B$ to the discharge $ETO_A$, and "a"=0.52, that the occupation ratio of the adsorption phases in the chambers Middle/Discharge is 5.0/1; for "a"=0.55, a ratio of 3.8/1 is calculated and for "a"=0.60 a ratio of 2.7/1. The final feed-back of component A and/or B at $EEO_A$ and/or $EEO_B$ prevents this concentration gradient and keeps an essentially constant loading of the separation phases over the entire length of the separation section. This results in optimal utilization of the separation phases over the total length of the separation section.

2. Improvement of the distribution coefficients "a" and/or "b" (so-called "displacement effect"): If the amount of component A introduced in the feed-stream is chosen such that nearly all yet available locations on $Ph_A$ which energetically favor component A, are in fact occupied by component A, then a small, added excess of component A competes with component B for those locations which energetically favor component A and displaces component B further from the separation phase $Ph_A$ ("displacement effect"). This effect is especially evident for those separation phases with discrete adsorption or inclusion locations, e.g. for cyclodextrins etc.

Combination of the two effects (1) and (2) results in a markedly increased separation productivity and markedly improved separation efficiency. Mathematical calculations, for e.g. "a"=0.51 and five distribution steps from the middle to the discharge (n=5), indicate a significant increase in purity.

Preferably the feed-back of the pure components A and/or B is done with recycle to feed-back of a part of the amounts in components A and/or B withdrawn at the discharge systems.

As a rule, suitable sorption agents are the same sorption agents utilized in the process of PCT Application WO 92/16275. These sorption agents differ from each other in e.g. polarity, geometric arrangement of the bonding functionalities, pore size, viscosity, temperature and/or electric charge.

In an embodiment of the process according to the invention, the temperatures of the sorption agents may be different and/or a temperature gradient existing in the direction of the separation section.

The separation productivity of a given cylinder stack formed by cylindrical disks $Z_A$ and $Z_B$ is directly proportional to the time needed for the equilibration of two systems. For cylindrical disks with only low height (especially from 0.1 to 2 mm), it is possible to effect exchange by diffusion alone. It is, however, preferred according to the invention to significantly foreshorten the equilibration time by suitable provisions to agitate the gap medium (transport phase) in axio-parallel direction.

It is thus preferred according to the invention, to establish a flow of the gap medium by means of a circulation system 136. In principle, circulation systems can also be used according to this invention as those utilized in the process of PCT Application WO 92/16275. This is also true for other process and equipment characteristics, corresponding to criteria in WO 92/16275, such as e.g. sorption agents, as well as charging and discharging systems.

The following circulation systems are preferred according to the invention:

(A) Open systems

If the number of cylindrical disks $Z_A$ and $Z_B$ is large and the concentration of separable material in the gap phase relatively small, then a closed circulation system can possibly be avoided. An axial movement of the gap medium can be achieved with a single, uniform stream of that gap medium by admitting it simply on one side or alternatingly on both sides of the stack formed by the cylindrical disks $Z_A$ and $Z_B$. This eliminates the need for a multiplicity of parallel pumping circuits. In this case, however, additional cylindrical disks $Z_A$ and $Z_B$ are required at the ends, if the process material migrating beyond the last cylindrical disk $Z_A$ and $Z_B$ is to be retained. A concentration gradient is also to be expected at the ends, which may significantly deteriorate the separation result.

(B) Closed systems

Closed systems for use according to the invention are:

(a) so-called oscillating systems, as e.g. a rubber lamellar pump which will be described later.

(b) circulating systems

A circulating system preferred according to the invention is provided by a friction pump featuring the gap of a rotating double disk (double disk gap friction pump), which will be described later.

One of these pump constructions is employed in preference, when many individual segments of the cylindrical disks $Z_A$ and $Z_B$ have to be circulated at a low pressure differential. Alternate, possible circulation systems include known pump constructions, such as e.g. piston or membrane pumps, potentially driven by a common shaft, or peristaltic pumps.

It is also possible to perform the process with a simulated counter movement by means of suitable valve regulation.

In this modification, an appropriate valving scheme controls the flow between vessels containing separation medium $Ph_A$ and vessels containing separation medium $Ph_B$, to simulate the sequence in which the individual structural elements, e.g. segments of two or several cylindrical disks $Z_A$ and $Z_B$, are superimposed and mutual equilibration by the counter-rotation of $Z_A$ and $Z_B$.

The process according to the invention is then characterized in that the individual segments in the rotating cylindrical disks 134, 135 ($Z_A$ and $Z_B$) are replaced by corresponding vessels 231 and 232, which contain the separation media $Ph_A$ and $Ph_B$ and are stationary, and in that the counter-rotational movement is simulated by suitable valving regulation between the vessels with separation medium $Ph_A$ and those with $Ph_B$.

Figure 15:
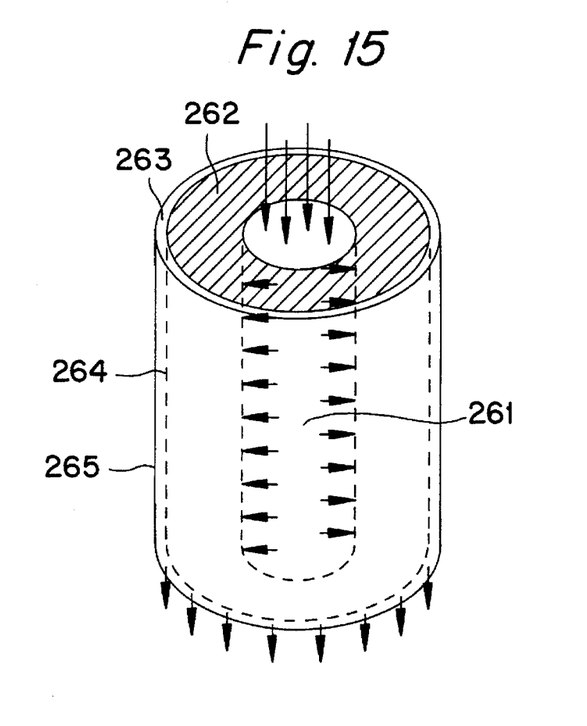
FIG. 15: Schematic and perspective presentation of a stationary vessel according to the invention.

The working arrangement is then one with a series of stationary vessels 231 with $Ph_A$ and a series of stationary vessels 232 with $Ph_B$. These stationary vessels with $Ph_A$ and $Ph_B$ consist e.g. of a hollow cylinder 262, which is permeable to the gap medium and is filled with the separation medium $Ph_A$ or $Ph_B$. The hollow cylinder 262 itself is located inside a tube 265 with a slightly larger diameter. Both hollow cylinder and outer tube are of the same length, and the two ends of the tube are each closed by a cover. One of these bears in its middle an inlet pipe leading into the interior 261 of the hollow cylinder, while the other cover bears an outlet between the outer wall of the hollow cylinder and the inner wall of the outer tube. With this arrangement, the gap medium containing the process material (feed stream to be separated) is introduced to the interior of the hollow cylinder containing $Ph_A$ or $Ph_B$, resp., flows through it in radial direction, and is then diverted through the gap 263 between the outer tube and the hollow cylinder.

In this manner it is achieved that the gap medium flows through a relatively thin layer of $Ph_A$ with essentially uniform thickness, and only then comes in contact again with the complimentary phase $Ph_B$ contained in that hollow cylinder which has just before been equilibrated with the hollow cylinder containing $Ph_A$. At the same time, it is possible with this arrangement to increase the amounts of separation medium $Ph_A$ and/or $Ph_B$ almost at well, by enlarging the diameter and the height of the hollow cylinders.

The stationary vessels are equilibrated with each other in the correct sequence, preferably by means of a "valve matrix" or a "3-disk-counter current-simulation-valve" according to the invention.

A "valve matrix" indicates e.g. a double matrix (one for the feed lines to, and a parallel one for the return lines from the individual circulation loops), each containing "n"×"n" 3-way valves, to equilibrate "n" individual, fixed vessels of $Ph_A$ with "n" individual, fixed vessels of $Ph_B$, and additionally 4×"n" 4-way valves for the charging and discharging steps. Thus e.g., each vessel with $Ph_A$ is connected in its feed line and its parallel return line to "n" 3-way valves arranged in series. (Only one exit is needed from the last 3-way valve in the valve chain thus formed of a vessel with $Ph_A$.) The second exit of each of these 3-way valves is connected to the respective feed or return lines of the vessels with $Ph_B$. An additional 4-way valve is located in each feed and return line to the vessels with $Ph_A$ and/or $Ph_B$, for the charging and discharging steps.

The required total number of valves (for the above case: 2×"n"×"n"+4×"n") can be reduced substantially by suitable control logistics. The overall number of required valves can be further lowered dramatically, when instead of 3-way valves (i.e. valves with 1 entrance, 2 exits) valves with 3 or more exits are used.

"3-disk-counter current-simulation-valve"

Figure 13:
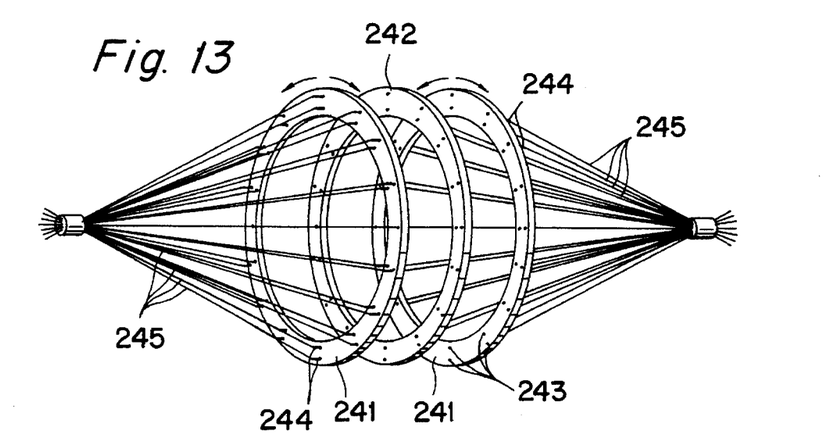
FIG. 13: Schematic and perspective presentation of a "3-disk-counter current-simulation-valve" according to the invention.

This valve consists of three, concentrically superimposed, ring-shaped disks 241, 242 having the same number of pairs of adjacent holes ("double holes"), which are arranged in concentric, equi-distant positions congruent in all three disks. The double holes 243 of the two outer disks 241 of the three-disk-cylinder thus formed, are connected on their outboard sides through a feed and return line each with the stationary vessels, and all vessels with the separation medium $Ph_A$ are connected to one outer disk, while all vessels with the separation medium $Ph_B$ are connected to the other outer disk of the valve.

The double holes of the two outer disks are attached on their outboard sides to suitable lines (e.g. elastic hoses) in such a way, that allows rotation of these disks around the axis of the three-disk-cylinder in both directions by 180 degrees each. For every equilibration step, both outer disks are turned in opposite direction and advanced by e.g. one hole position each (or several, and if appropriate, one outer disk by a number of hole positions that is different from that of the other disk), while the middle disk with the inlet and outlet connections 256 is not moved.

The row of double holes in the middle disk 254 connects the rows of double holes in the outer disks, with the exception of those double holes through which a charging or discharging of the stationary vessels is to occur. In these holes, passage is blocked approximately midway and the connector ends 258 thus formed are each provided with a hose connection 256 lying radially in the plane of the disk.

Figure 14A:
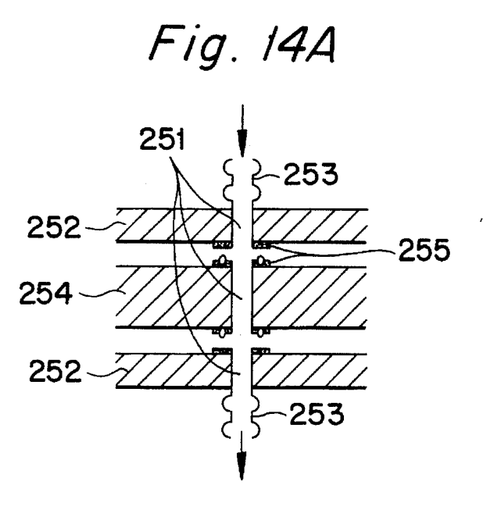
FIGS 14a and 14b: Schematic presentation of the bores in the "3-disk-counter current-simulation-valve", in cross-section.

The sealing of the three disks in a position, where the rows of double holes are congruently superimposed, is effectively done with O-ring seals 255 around the individual holes 251, or any other known sealing techniques. The outer disks are turned in counter-rotation, e.g. by one hole position for each equilibration step, and any desired position of the outer disks can be established by turning the disks from zero to 180 degrees in one or the other direction. The middle disks are normally not moved.

In principle, the middle disk can also be replaced by suitable valves (e.g. 4-way valves) positioned in the feed and return lines of the stationary vessels, and suitable control logistics for these charging and discharging valves. Thus the valve regulation arrangement then consists of one "2-disk-counter current-simulation-valve", i.e. the two outer disks of the "3-disk-counter current-simulation-valve", and 2×"n" 4-way valves for the lines to "n" vessels with $Ph_A$ and 2×"n" 4-way valves for the lines to "n" vessels with $Ph_B$, and the associates control logistics.

Figure 2:
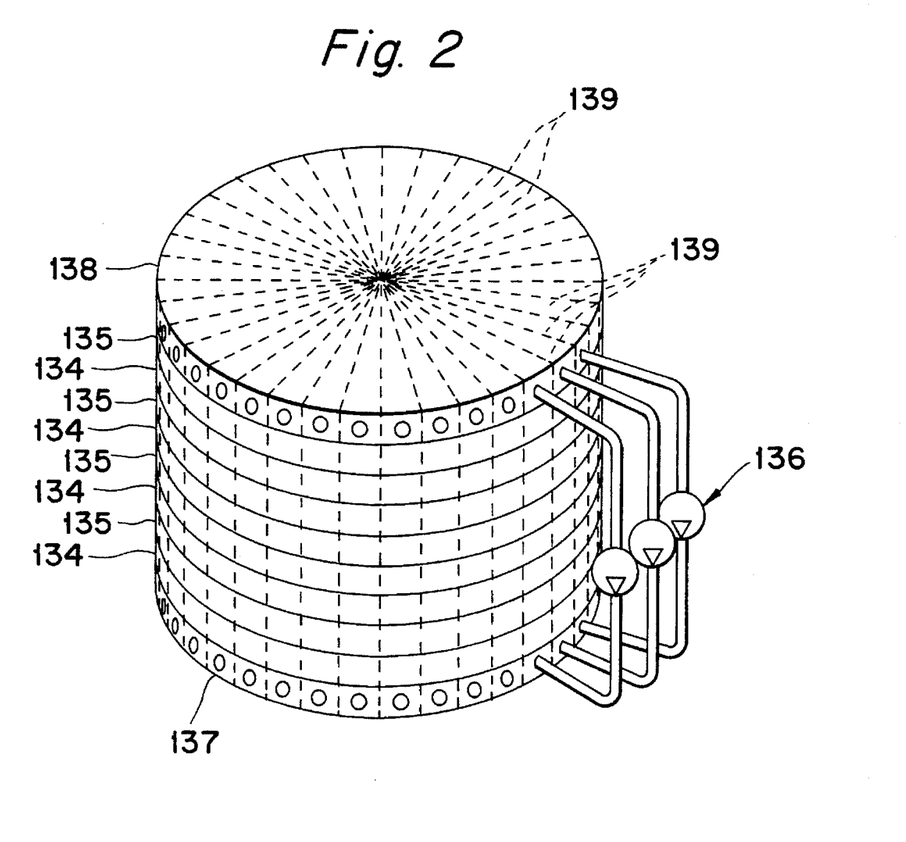
FIG. 2: A schematic perspective view of a device according to this invention.
Figure 8:
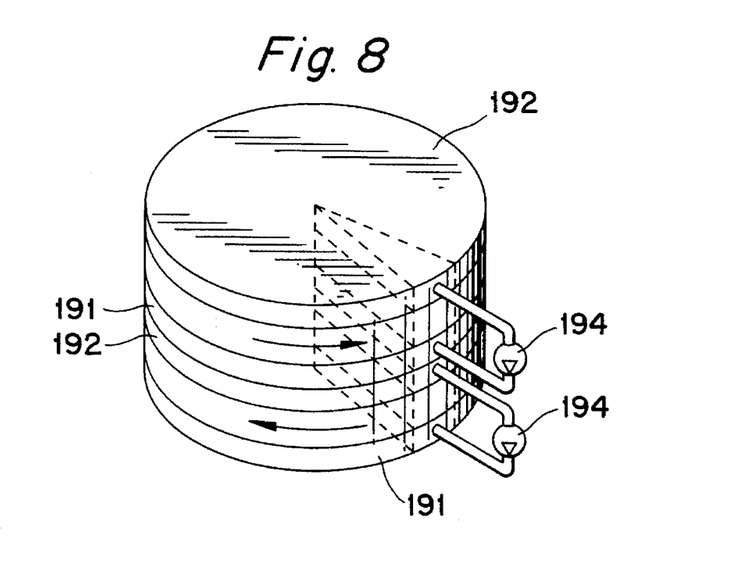
FIG. 8: Schematic presentation of a device according to the invention with the associated charging, discharging and circulating systems.
Figure 11:
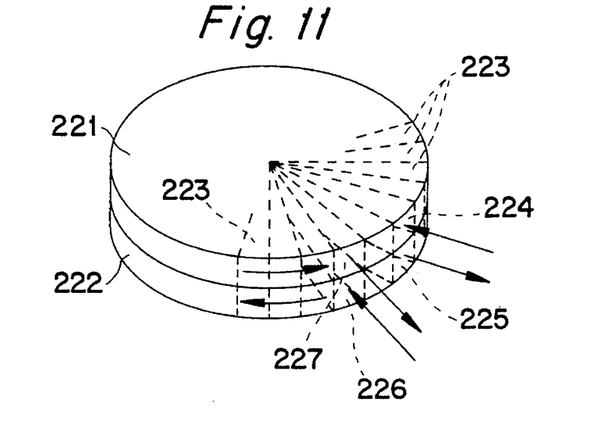
FIG. 11: Schematic presentation of feed system used according to the invention, in a perspective view.

These arrangements allow exactly the same sequence of equilibration, charging and discharging for stationary vessels, as was previously depicted in FIGS. 2, 8, and 11 for rotating segments.

Figure 12:
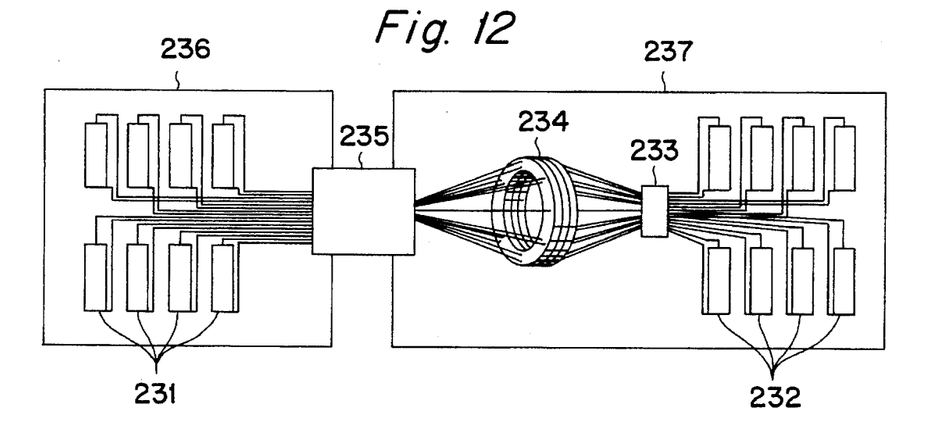
FIG. 12: Schematic and perspective presentation of a separation unit according to the invention, with stationary vessels, "3-disk-counter current-simulation-valve" and heat exchanger system.

The embodiment of the invention using stationary vessels and simulated counter movement is especially suitable for separations on a larger scale and those, where the subdivision of the cylindrical disks $Z_A$ and $Z_B$ into a small number of structural elements, e.g. segments, is sufficient. It has the added advantage that only comparatively small technical effort is required to maintain the vessels containing $Ph_A$ at one temperature $T_A$, and the vessels containing $Ph_B$ at a temperature $T_B$ (which may, if appropriate, be different from $T_A$). This may be accomplished, e.g. by incorporating heat exchangers 235 into the connections of the vessels with $Ph_A$ to those vessels with $Ph_B$.

In carrying out the process, according to the invention, with the simulated counter-current movement, it is especially beneficial to use one of the circulating systems described previously under (B) (b), e.g. one of the pumps described there.

In the process according to the invention, with the simulated counter-current movement, it is possible likewise to increase the separation productivity and improve the separation efficiency by utilizing the previously described "displacement effect" with a final feed-back of the pure components or mixtures enriched in the pure components.

A subject of this invention is also a device for carrying out the process according to the invention. The device according to the invention is characterized in that it comprises at least two or several hollow, concentrically superimposed cylindrical disks (134, 135) $Z_A$ and $Z_B$, which are filled with structural elements and contain the separation media $Ph_A$ and $Ph_B$, which in turn are composed of or contain the sorption agents (1, 2), and in that neighboring cylindrical disks $Z_A$ and $Z_B$ are alternately arranged and turn in opposite directions on a common axis, and that it has charging provisions (191) for introducing the mixture of substances to be separated, and discharge provisions (192) for the recovery of the separated fractions of the mixture.

Suitable embodiments of the device according to the invention have already been described previously, in the context of carrying out the process.

Another subject of this invention is a new rubber lamellar pump, as can be utilized according to the invention in one of the previously described closed systems of circulation arrangements.

Figure 9:
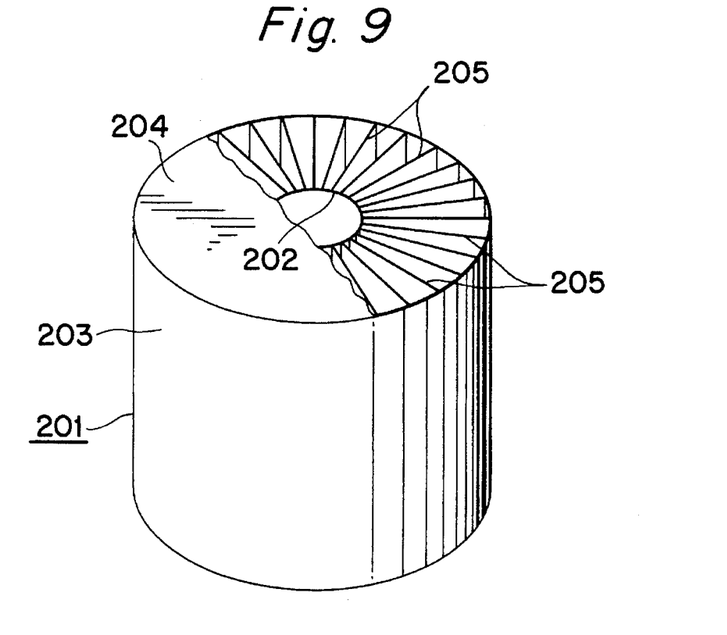
FIG. 9: Schematic presentation of a rubber lamellar pump according to the invention, in a perspective view.

The rubber lamellar pump according to the invention comprises a cylinder 201, made from thin, elastic wall material, and an inner axial tube 202, the outer wall of the inner axial tube and the elastic cylinder wall 203, as well as the front wall 204 being connected by elastic lamellae.

The entire body of the rubber lamellar pump is thus subdivided into many gas- and liquid-tight segments of essentially equal size, which only on their underside have slits open to the cylinder stack formed from the cylindrical disks $Z_A$ and $Z_B$. If the cylindrical disks feature a segmentation as e.g. shown in FIG. 17, it is preferable to give the segments of the rubber lamellar pump a congruent shape. Preferably both ends of the cylinder stack are equipped with a rubber lamellar pump of this type. By a counter-rotational turning of the outer front walls of the rubber lamellar pumps, the lamellar volumes are each decreased somewhat, and then enlarged again upon the back turn. An oscillation movement of the gap medium can be achieved in this manner.

The rubber lamellar pumps are especially suitable for a process and/or a device according to the invention, for the separation of a mixture of substances, in which the volume of the gap medium per cylindrical disk $Z_A$ and $Z_B$ is small in comparison to the volume of the individual rubber lamellae in the rubber lamellar pump. The rubber lamellar pump according to the invention is, therefore, utilized in preference for very low heights of the cylindrical disks $Z_A$ and $Z_B$. It is also utilized for the case of a subdivision of the cylindrical disks $Z_A$ and $Z_B$ into very many structural elements, especially segments.

Suitable materials of construction for the rubber lamellar pump according to the invention are sufficiently elastic materials, which preferably are inert to the media flowing through the cylindrical disks $Z_A$ and $Z_B$, such as e.g. rubber.

Also a subject of the present invention is a new friction pump through the gap of a rotating double disk (double disk gap friction pump).

Figure 10A:
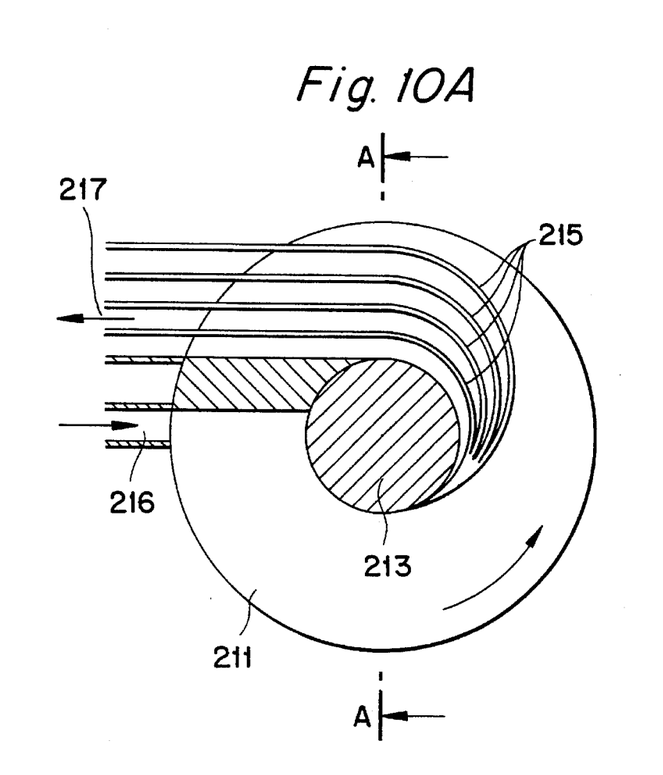
FIGS. 10a and 10b: Schematic presentation of a double disk gap friction pump according to the invention, in a perspective view, and in cross-section, respectively
Figure 10B:
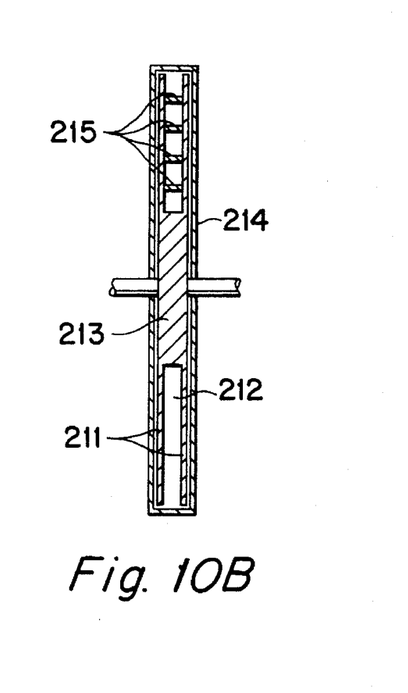

The double disk gap friction pump according to the invention comprises a double disk 211 with a narrow gap 212, which is mounted on a shaft 213 and enclosed on both sides by a tight-fitting housing 214, and features a peeling device 215 protruding into the gap 212 up to the shaft 213, and arranged ahead and behind the peeling device 215 bears inlet connector 216 and outlet connector 217. The width of the double disk gap friction pump according to the invention may be very small, and is preferably 3 to 100 mm; due to this narrow width, many double disk gap friction pumps can be arranged on the same shaft, and this pump type is, hence, especially suited for simultaneous circulation against a small pressure differential, of all the segments or stationary vessels with large volumes of gap medium.

Suitable materials of construction for the double disk gap friction pump according to the invention are metallic materials such as steel, brass, aluminum etc.

In the following, functional embodiments of this invention are described with reference to the respective drawing and serve as examples, without constituting limits for the invention.

Figure 1:
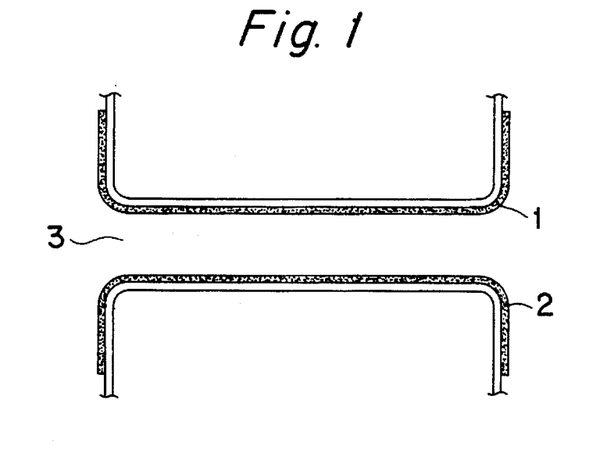
FIG. 1: A schematic view of a device in cross-section.

FIG. 1 shows a schematic representation of a device, in cross-section: The separation chamber 3 is located between the surfaces of the sorption agents 1 and 2.

FIG. 2 shows a schematic and perspective representation of a device according to the invention. Superimposed cylindrical disks (134, 135) $Z_A$ and $Z_B$, containing the separation media $Ph_A$ and $Ph_B$, are arranged in alternation and can rotate around a common axis in opposite direction to each other; a charging disk 137 and a discharging disk 138 are not moved; the device contains a circulation system 136, and each segment 139 has its own assigned circulation system 136.

Figure 3:
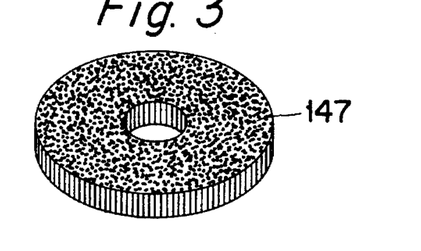
FIGS. 3 to 7: Modifications of configurations for the structural elements present in the cylindrical disks $Z_A$ and $Z_B$.

FIG. 3 shows an embodiment according to the invention, in which the structural elements present within the cylindrical disks have the form of fibers and/or small rods 147.

Figure 4:
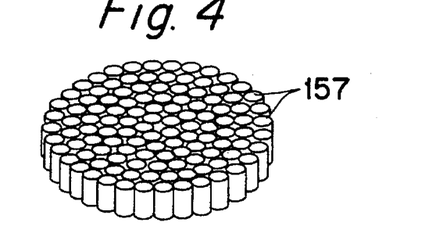

FIG. 4 shows an embodiment according to the invention, in which the structural elements have the form of capillaries or thin tubes 157.

Figure 5:
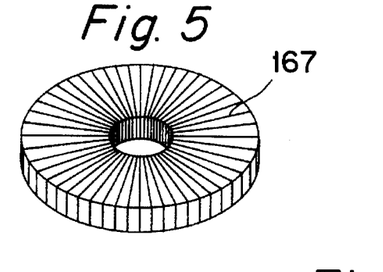

FIG. 5 shows an embodiment according to the invention, in which the structural elements are formed by lamellae 167.

Figure 6:
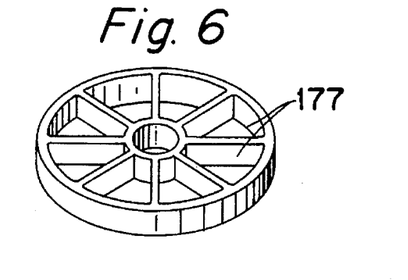

FIG. 6 shows an embodiment according to the invention, in which the structural elements take the form of pie segments 177.

Figure 7:
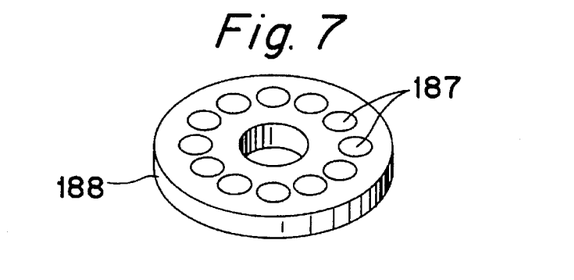

FIG. 7 shows an embodiment according to the invention, in which the structural elements have the shape of circular segments 187 within the cylindrical disks 188.

FIG. 8 shows a schematic representation of a device according to the invention with charging- 191 and discharging- 192 systems in the form of static cylindrical disks. The cylindrical disks 191, which are part of the charging system, are connected by circulation systems 194 to the cylindrical disks 192, which are part of the discharging system.

FIG. 9 shows a schematic representation of a rubber lamellar pump according to the invention, in perspective view. The rubber lamellar pump comprises a cylinder 201, made from a thin, elastic wall material, and an inner axial tube 202; the outer wall of the inner axial tube is connected with the elastic cylinder wall 203 and with the enclosure top wall 204 by a multiplicity of elastic lamellae 205.

FIG. 10a shows a schematic representation of a double disk gap friction pump according to the invention, from a top view, while FIG. 10b shows a schematic representation of a section in the plane A—A of FIG. 10a. A double disk 211 with a narrow gap 212 is resting on a shaft 213 and is enclosed on both sides and cylindrically around the circumference of the double disk by a tight fitting housing 214, which contains a peeling device 215. This device 215 extends into the gap 212 up to the shaft 213 and fits in the closest possible way between the rotating disks. Inlet nipples 216 and outlet nipples 217 are arranged before and after the peeling device.

FIG. 11 shows a schematic and perspective representation of a feed system according to the invention; a cylindrical disk 221 containing the separation medium $Ph_A$ is located next to a cylindrical disk 222 rotating in the opposite direction and containing the separation medium $Ph_B$. Into the cylindrical disk 221 is fed the component B (preferably as pure component B) at segment 224 (=charging location $ETO_B$), which is situated opposite to the discharge location $ATO_B$ 225 for component B. At the same time, pure component B is discharged from cylindrical disk 222 at the corresponding segment 225 (=discharge location $ATO_B$) located directly below. In the same manner, component A (preferably as the pure component A) is fed to the cylindrical disk 222 via the charging location $ETO_A$ 226, while pure component A is discharged from cylindrical disk 221 at the corresponding segment 227 (=discharge location $ATO_A$) located directly above. The schematic representation shows a multiplicity of distribution steps (segments) 223 for the component A and the component B.

FIG. 12 is a schematic and perspective representation of a separation unit according to the invention, with fixed installation of vessels 231, containing $Ph_A$, and 232, containing $Ph_B$, and having a "3-disk-counter current-simulation-valve" 234 and a system of heat exchangers 235. In each case, the medium in the intermediate space is circulated in individual closed loops by the circulation pump 233 between a stationary vessel 231 with $Ph_A$ and a stationary vessel 232 with $Ph_B$, through the "3-disk-counter-current-simulation-valve" 234 and a heat exchanger 235. In this manner, one vessel each with $Ph_A$ is equilibrated with one vessel each with $Ph_B$, and then the outer disks of the "3-disk-counter current-simulation-valve" are each advanced e.g. by one double hole position, to form new individual circulation loops in which the medium of intermediate space is again circulated between one vessel each with $Ph_A$ and with $Ph_B$. During this operation, a system of heat exchangers installed between the vessels containing $Ph_A$ and the vessels containing $Ph_B$ makes it possible to maintain the fixed vessels with $Ph_A$ in area 236 at a temperature $T_A$ and the fixed vessels with $Ph_B$ in area 237 at a temperature $T_B$. The sequence of equilibrations between one vessel each with $Ph_A$ and one vessel with $Ph_B$, which is generated in this manner, corresponds to the sequence of equilibrations obtained between individual segments of two counter-rotating disks.

FIG. 13 is a schematic and perspective representation of a "3-disk-counter current-simulation-valve" according to the invention, which shows the two outer disks 241 and the inner disk 242, with their matching double holes 243, which are arranged concentrically and at uniform distances. The double holes of the outer disks are connected at their outboard sides to attachment nipples 244, from where elastic hoses form feed- and return-lines 245 to a stationary vessel. The entire interconnection is made in such a manner that rotation of the outer disks by 180 degrees is possible in both directions. In each equilibration position, the holes of all three disks are superimposed and thus form the desired channels. For reasons of clarity, the distance between the three disks has been depicted in extreme magnification. In reality, the disks contact each other.

Figure 14B:
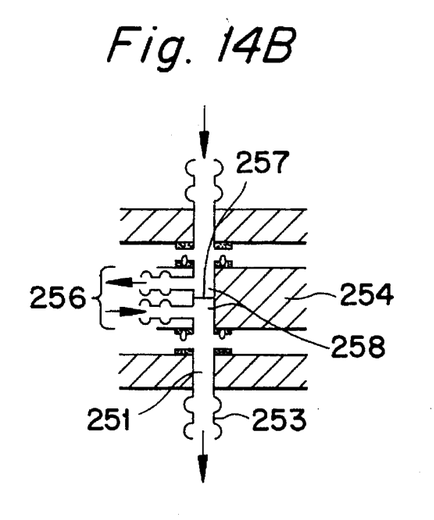

FIGS. 14a and 14b show a schematic representation of the bore holes in the "3-disk-counter current-simulation-valve", shown in cross-section.

FIG. 14a shows one hole 251 each in the two outer disks 252, with the connector 253 (e.g. hose nipples) and a hole 251 in the middle disk, as viewed in cross-section. A seal is achieved e.g. by a suitable O-ring construction 255.

FIG. 14b shows one hole 251 each in the two outer disks and a charging-/discharging- adaptor 256 in the middle disk 254, with the connectors 253 (e.g. hose nipples), as viewed in cross-section. The charging-/discharging- adaptor 256 blocks the passage through the middle disk 254, by the barrier 257, in approximately mid position. The channel ends 258 thus formed are connected to the charging and discharging lines, respectively, by means of the connectors 253 (e.g. hose nipples). For reasons of clarity, the distance between the three disks has been depicted in extreme magnification. In reality, the disks contact each other.

FIG. 15 is a schematic and perspective representation of a vessel in stationary installation, according to the invention. The medium of the intermediate space is directed to the interior 261 of the hollow cylinder 262 containing the separation medium $Ph_A$ or $Ph_B$, respectively, flows through this material in a radial direction and then out through the gap 263 between the outer wall 264 of the hollow cylinder and the outer tube 265 of equal length. The covers of the vessel are not shown.

I claim:

1. A process for the separation of a mixture of substances by sorption of the components of the mixture on two different sorption agents, which can be adjusted individually and separately from each other in their sorption properties and by passing through a separation section of the sorption agents with the ab- or adsorbed components of the mixture, according to which process the mixture to be separated is introduced into a separation chamber between surfaces of the sorption agents, and a gap medium flows between the sorption agents in which the components of the mixture can be dissolved and/or dispersed and/or evaporated, and whereby phases containing the sorption agents move in directions opposite to each other, and in which the separated components of the mixture held on the sorption agents are recovered after they pass through the separation section, whereby the separation chamber is formed by two or more hollow cylindrical disks $Z_A$ and $Z_B$, which are filled with structural elements and are concentrically superimposed and contain separation media $Ph_A$ and $Ph_B$, consisting of or containing the sorption agents, and whereby the cylindrical disks $Z_A$ and $Z_B$ are alternately arranged and turn in opposite directions on a common axis.

2. A process according to claim 1, wherein the structural elements have the form of fibers and/or thin rods or of capillaries or thin tubes.

3. A process according to claim 1, wherein the structural elements have the form of lamellae.

4. A process according to claim 1, wherein the structural elements have the form of segments.

5. A process according to claim 4, wherein the segments possess the shape of pie-segments or circular segments.

6. A process according to claim 4, wherein the segments are filled with particulate, fibrous, capillary- or foil-shaped separation and/or carrier materials, which consist of the sorption agents and/or have surfaces bearing the sorption agents.

7. A process according to claim 6, wherein the separation and/or carrier materials are silica gels, sand, diatomaceous earth, calcined clay, polymeric particles, polymeric fibers, cotton, wool, nylon fibers, glass wool, capillary tubes of glass or organic polymers and/or glass beads.

8. A process according to claim 1, wherein the cylindrical disks are turned discontinuously.

9. A process according to claim 8, wherein the cylindrical disks $Z_A$ and $Z_B$ turn discontinuously and wherein the structural elements are formed by subdividing the cylindrical disks $Z_A$ and $Z_B$ into corresponding segments, such that the corresponding segments are superimposed on each other during a rest phase (equilibration phase) of the discontinuous turning.

10. A process according to claim 1, wherein the mixture of substances to be separated is introduced through a stationary cylindrical charging disk and the discharge of the components (fractions) of the separated mixture of substances from the sorption agents is accomplished through a stationary cylindrical discharging disk, which stationary cylindrical disks are disposed between the cylindrical disks $Z_A$ and $Z_B$.

11. A process according to claim 10, wherein the cylindrical disks possess the same segmentation as the cylindrical disks $Z_A$ and $Z_B$.

12. A process according to claim 11, whereby, for separation of a mixture consisting of the components A and B, the component A and/or the component B is introduced to a segment lying opposite to a discharge location for component A and/or to a segment lying opposite to a discharge location for component B.

13. A process according to claim 12, wherein a portion of the amount of the component A and/or B withdrawn from the discharging system is returned as component A and/or B.

14. A process according to claim 10, wherein the flow of the gap medium is produced with a circulation system.

15. A process according to claim 14, wherein each segment of the charging and the discharging disks is associated with one circulation system.

16. A process according to claim 14, wherein the circulation system is an oscillating system or a recirculation system.

17. A process according to claim 1, wherein the temperature of the sorption agents can be different and/or that a temperature gradient exists in the direction of the separation section.

18. A process according to claim 1, wherein the individual segments of the turning cylindrical disks are replaced by corresponding stationary vessels containing the separation media $Ph_A$ and $Ph_B$, and the turning in opposite directions is simulated by a suitable valving control between the vessels with the separation medium $Ph_A$ and the vessels with the separation medium $Ph_B$.

19. A process according to claim 18, wherein the stationary vessels consist of a hollow cylinder containing the separation medium $Ph_A$ and $Ph_B$ and being permeable for the gap medium, said hollow cylinder being located inside a tube of equal length, and the common ends of the hollow cylinder and the tube each being closed by a cover, and where an inlet provision leads into the interior of the hollow cylinder and an outlet provision leads from between the outer wall of the hollow cylinder and the inner wall of the tube to the exterior, such that the gap medium with the components of the mixture is introduced into the interior of the hollow cylinder with $Ph_A$ or $Ph_B$, flows through it radially and is then discharged through the gap between the outer tube and the hollow cylinder.

20. A process according to claim 18, wherein the valving control is achieved with a valve matrix, consisting of valves with 1 or 2 inlets and 1, 2, 3 or more exits, a suitable interconnection of the valves among each other and with the vessels containing $Ph_A$ and $Ph_B$ and a suitable valve control logic, or is achieved with a 2- or 3-disk-counter- current-simulation valve.

21. A process according to claim 18, wherein the valving control is achieved by three concentrically superimposed, ring-shaped disks featuring an equal number of pairs of two neighboring holes each ("double holes") which are in concentric, congruent and equidistant position, and where the double holes of the two outer disks in the three-disk cylinder thus formed, each are connected on their outboard sides by means of an inlet- and outlet conduit each, to the stationary vessels, and where all the vessels containing $Ph_A$ are connected to one outer disk and all vessels containing $Ph_B$ are connected to the other outer disk.

22. A process according to claim 21, wherein the double holes of the two outer disks on their outboard sides are connected with suitable hoses in such a manner as to allow a rotation of these disks around the axis of the three-cylinder- disk in both directions by 180 degrees each, and in that for each equilibration step, the two outer disks are advanced in opposing directions by one or more hole positions, and the number of these positions can be different for the upper and the lower disk, while the double holes in the middle disk feature charging and discharging connectors in appropriate locations, and are configured such that the holes are blocked approximately midway thus forming sleeve ends for the connectors, and that the middle disk is normally not moved.

23. A process according to claim 21, wherein the middle disk with its suitably located inlet- and outlet-connectors is replaced by suitable valves which are installed in the charging and discharging lines to and from the stationary vessels, and an appropriate control logic for these inlet and outlet valves.

24. A process according to claim 18, wherein the stationary vessels with separation medium $Ph_A$ are maintained at a certain temperature $T_A$ and the stationary vessels are maintained with separation medium $Ph_B$ at a certain temperature $T_B$, and, if appropriate, suitable heat exchangers are installed in the connector lines between the vessels with $Ph_A$ and $Ph_B$.

25. A device for the separation of a mixture of substances by sorption of the components of the mixture on two different sorption agents, said device comprising two or more hollow, concentrically superimposed cylindrical disks $Z_A$ and $Z_B$, which are filled with structural elements which contain separation media $Ph_A$ and $Ph_B$ consisting of or containing the sorption agents, and in which the cylindrical disks $Z_A$ and $Z_B$ are alternately arranged and turn in opposite directions on a common axis, and charging provisions for introducing the mixture of substances to be separated, and discharging provisions for the recovery of the separated substances of the mixture.

* * * * *